(12) United States Patent
Zhang et al.

(10) Patent No.: US 10,959,974 B2
(45) Date of Patent: Mar. 30, 2021

(54) INGENOL COMPOUNDS AND USE THEREOF IN ANTI-HIV LATENCY TREATMENT

(71) Applicant: SHANGHAI XIN HAO BIOLOGICAL TECHNOLOGY COMPANY, Shanghai (CN)

(72) Inventors: Longfei Zhang, Shanghai (CN); Pengfei Wang, Shanghai (CN); Zhongjun Ma, Shanghai (CN); Huanzhang Zhu, Shanghai (CN)

(73) Assignee: SHANGHAI XIN HAO BIOLOGICAL TECHNOLOGY COMPANY, Shanghai (CN)

( * ) Notice: Subject to any disclaimer, the term of this patent is extended or adjusted under 35 U.S.C. 154(b) by 0 days.

(21) Appl. No.: 16/067,400

(22) PCT Filed: Feb. 22, 2016

(86) PCT No.: PCT/CN2016/074282
§ 371 (c)(1),
(2) Date: Dec. 3, 2018

(87) PCT Pub. No.: WO2017/113489
PCT Pub. Date: Jul. 6, 2017

(65) Prior Publication Data
US 2019/0083443 A1    Mar. 21, 2019

(30) Foreign Application Priority Data
Dec. 31, 2015   (CN) .......................... 201511031304.5

(51) Int. Cl.
| | |
|---|---|
| *A61K 31/23* | (2006.01) |
| *A61K 31/357* | (2006.01) |
| *C07D 317/72* | (2006.01) |
| *C07D 493/10* | (2006.01) |
| *C07C 67/28* | (2006.01) |
| *C07C 67/48* | (2006.01) |
| *C07C 69/33* | (2006.01) |
| *A61P 31/18* | (2006.01) |

(52) U.S. Cl.
CPC ............ *A61K 31/23* (2013.01); *A61K 31/357* (2013.01); *A61P 31/18* (2018.01); *C07C 67/28* (2013.01); *C07C 67/48* (2013.01); *C07C 69/33* (2013.01); *C07D 317/72* (2013.01); *C07D 493/10* (2013.01)

(58) Field of Classification Search
CPC ...... A61K 31/23; A61K 31/357; C07C 67/28; C07C 67/48; C07C 69/33; A61P 31/18; C07D 317/72; C07D 493/10
See application file for complete search history.

(56) References Cited

U.S. PATENT DOCUMENTS

| | | | |
|---|---|---|---|
| 2005/0026902 A1* | 2/2005 | Maziasz | ................. A61K 45/06 514/217 |
| 2015/0030638 A1* | 1/2015 | Pianowski | ............. A61K 45/06 424/283.1 |

FOREIGN PATENT DOCUMENTS

| | | |
|---|---|---|
| CN | 104136081 A | 11/2014 |
| JP | 08245379 | * 9/1996 |

OTHER PUBLICATIONS

International Search Report, dated Oct. 10, 2016, for International Application No. PCT/CN2016/074282, 10 pages.

* cited by examiner

*Primary Examiner* — Timothy R Rozof
(74) *Attorney, Agent, or Firm* — Seed IP Law Group LLP

(57) ABSTRACT

Provided in the present invention are ingenol compounds and a use thereof in preparing an anti-HIV latency drug. In particular, provided in the present invention is a use of ingenol compounds and pharmaceutically acceptable salts thereof for preparing a drug for: (a) intervening with HIV viral latency; (b) activating an HIV virus that has been integrated into mammalian genomes; and/or (c) inducing the expression of the dormant HIV provirus in infected cells. The compounds of the present invention may also be used in combination with antiretroviral drugs to accelerate the removal of latent viral reservoirs.

18 Claims, 3 Drawing Sheets

INGENOL COMPOUNDS AND USE THEREOF IN ANTI-HIV LATENCY TREATMENT

TECHNICAL FIELD

The present invention relates to the field of the medicine, in particular, to ingenol compounds and use thereof in anti-HIV latency treatment.

BACKGROUND TECHNOLOGY

Acquired immunodeficiency syndrome (AIDS) is a contagious disease that seriously endangers people's life and health caused by HIV infection. According to WHO statistics, there are more than 40 million AIDS patients worldwide, with 5 million new patients each year, while about 3 million deaths each year. At present, the main clinical treatment of AIDS is Highly active antiretroviral therapy (HAART), which not only effectively controls HIV replication, but also rebuilds the immune function of AIDS patients, thereby opening the door of hope for the treatment of AIDS. People have hoped that HAART can completely eliminate HIV in vivo, thereby achieving the goal of completely curing AIDS. However, subsequent practice has shown that although HAART can inhibit viral replication in patients at the largest extent, and reduce plasma viral load to levels not detected by conventional detection methods, there are still viruses in the infected body. Once drug treatment is stopped, the viral load will rebound to the pre-treatment level (Ho, D D Toward HIV eradication or remission: the tasks ahead. Science, 1998. 280: 1866-1867). One of the important reasons that HIV is difficult to be completely eliminated in vivo is that HIV-1 can hide in resting memory CD4+ T cells, which are produced by the transformation of a small number of HIV-infected activated CD4+ T cells. The integrated provirus thereof lacks transcriptional activity and therefore, will not be attacked by the immune system and antiretroviral drugs. Although the infected individual carries a small number of the latent infected cells, the attenuation rate is so slow that it is impossible to completely remove it only by HAART treatment during the individual lifetime. Therefore, HIV latently infected resting CD4+ T cells are the main part of the virus reservoir in the body, and they are also the huge obstacle for the complete elimination of HIV in clinical treatment [Finzi, D. et al. Latent infection of CD4+ T cells provides a mechanism for lifelong persistence of HIV-1, even in patients on effective combination therapy. Nature Med. 1999, 5, 512-517]. The molecular mechanism of the formation of HIV-1 latently infected cells is generally considered to be related with the chromatin state at the integration site, the presence of the inhibitory nucleosome nuc-1, the epigenetic modification represented by acetylation, and the host transcription factor such as NF-κ B, the viral transcriptional activator Tat and other factors [Coiras, M., M R et al. Understanding HIV-1 latency provides clues for the eradication of long-term reservoirs. Nat. Rev. Microbiol. 2009., 7:798-812.]. Based on this mechanism, some studies have proposed a therapeutic strategy for clearing latent virus reservoirs, which is to try to induce pro-virus expression of HIV latent-infected cells by drugs, and to re-activate their latent viruses, and at the same time, to combine high-efficiency anti-retroviral therapy with the following method: the activated latent infected cells is killed under the action of the human immune system, so that the removal of the virus reservoir is accelerated (Richman et al. The Challenge of Finding a Cure for HIV Infection, Science, 2009, 1304, 323). Although there are several treatment solutions in the clinic for the strategy, the results are still unsatisfactory, either the activator is ineffective, or it is effective but its toxic side effect is large. However in China, there are still no anti-AIDS new drugs with the independent intellectual property rights available on market. Therefore, it is of great significance to develop new intervention drugs with independent intellectual property rights, safe, effective and inexpensive to eliminate the HIV-1 virus reservoir.

As a unique medical resource in China, traditional Chinese medicine has attracted more and more attention from modern medicine because of the following advantages: wide varieties, wide clinical application, mild effect and few side effects and the like.

SUMMARY OF THE INVENTION

The object of the present invention is to provide a medicament having anti-HIV latent effect, in particular to the use of an ingenol compound and a derivative thereof for the treatment of anti-HIV latency.

In the first aspect, a use of a compound represented by formula I or a pharmaceutically acceptable salt is provided, for the preparation of a composition or formulation, and the composition or formulation is used for (a) interfering with the HIV virus latency; (b) activating a HIV virus that has been integrated into the mammalian genome; and/or (c) inducing the expression of a HIV provirus latent in an infected cell:

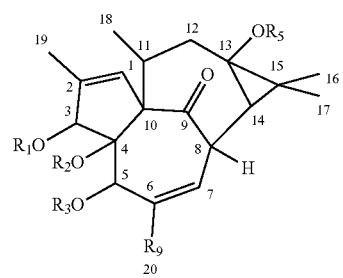

I wherein $R_1$ is selected from H, substituted or unsubstituted COCH$(CH_3)CH(CH_3)_2$ or substituted or unsubstituted OCC$_6H_5$;

$R_2$ is selected from H, substituted or unsubstituted COCH$(CH_3)CH(CH_3)_2$ or substituted or unsubstituted OCC$_6H_5$;

$R_3$ is selected from H, substituted or unsubstituted COCH$(CH_3)CH(CH_3)_2$ or substituted or unsubstituted OCC$_6H_5$;

$R_5$ is selected from H, COCH$_3$, OCH$_2$CH$_3$ or CO(CH$_2$)$_{10}$CH$_3$;

$R_9$ is selected from the group consisting of: CH$_2$OR$_4$ and —C(O)R$_{10}$; wherein $R_4$ is selected from H, COCH$_3$, OCH$_2$CH$_3$, CH$_2$CH$_3$, CO(CH$_2$)$_{10}$CH$_3$, or CO(CH$_2$)$_{14}$CH$_3$; $R_{10}$ is selected from the group consisting of: H, substituted or unsubstituted C$_1$-C$_6$ alkyl, C$_2$-C$_6$ alkenyl, C$_2$-C$_6$ alkynyl, C$_1$-C$_6$ alkoxy, —OH, C$_1$-C$_6$ ester group, and a combination thereof;

or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein the "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, $C_2$-$C_6$ alkynyl.

In another preferred embodiment, the "substituted" means being substituted with one or more substituents selected from the group consisting of: halogen, $C_1$-$C_4$ alkyl, $C_1$-$C_4$ haloalkyl, $C_2$-$C_4$ alkenyl, $C_2$-$C_4$ alkynyl.

In another preferred embodiment, any one group of $R_1$ and $R_2$, $R_2$ and $R_3$, $R_3$ and $R_9$ respectively and independently forms a 5-7 membered substituted or unsubstituted heterocycle containing 2-3 oxygen atoms and 0-1 heteroatoms selected from N or S.

In another preferred embodiment, any two groups of $R_1$ and $R_2$, $R_2$ and $R_3$, $R_3$ and $R_9$ respectively and independently form a 5-7 membered substituted or unsubstituted heterocycle containing 2-3 oxygen atoms and 0-1 heteroatoms selected from N or S.

In another preferred embodiment, the halogen is selected from the group consisting of: F, Cl, Br and I.

In another preferred embodiment, the compound is an optical isomer or a racemate.

In another preferred embodiment, the compound has a structure as shown in formula Ic or formula Id:

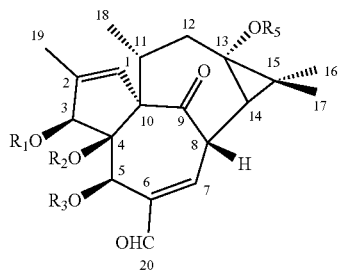

Ic

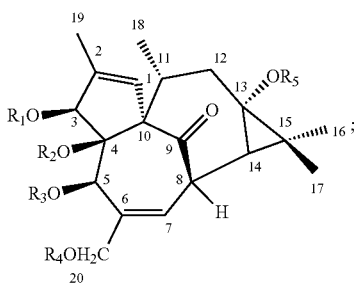

Id wherein $R_1$, $R_2$, $R_3$, $R_4$ and $R_5$ are defined as the first aspect of the present invention.

In another preferred embodiment, the composition or formulation is further used for (d) treating AIDS; and/or (e) treating AIDS in combination with an antiretroviral drug.

In another preferred embodiment, the "interfering with the HIV virus latency" comprises: inducing the HIV proviral expression in a latently infected cell of the HIV virus, and/or activating a latent HIV virus; and/or the treatment of AIDS comprises the treatment of anti-HIV latency.

In another preferred embodiment, the antiretroviral drug is selected from the group consisting of: a reverse transcriptase inhibitor, a protease inhibitor, a co-receptor antagonist, a retroviral integrase inhibitor, a viral adsorption inhibitor, and a specific viral transcriptional inhibitor, a cyclin-dependent kinase inhibitor, an anti-HIV antibody, and a combination thereof.

In another preferred embodiment, the compound of formula I, or a pharmaceutically acceptable salt thereof is chemically synthesized.

In another preferred embodiment, the compound of formula I, or a pharmaceutically acceptable salt thereof is extracted from a plant.

In another preferred embodiment, the "extracted" comprises extraction using a method selected from the group consisting of: solvent extraction, extraction method, and chromatography.

In another preferred embodiment, the plant comprises an Euphorbiaceae plant. In another preferred embodiment, the Euphorbiaceae plant comprises *Euphorbia kansui* T. N. Liou ex S. B. Ho.

In another preferred embodiment, the composition comprises a pharmaceutical composition, a food composition or a health care product composition.

In another preferred embodiment, the medicament further comprises an additional component selected from the group consisting of: an active ingredient of an anti-retroviral virus and an active ingredient that enhances immunity.

In another preferred embodiment, the pharmaceutical composition comprises (i) a compound of formula I or a pharmaceutically acceptable salt thereof; and (ii) a pharmaceutically acceptable carrier.

In another preferred embodiment, the component (i) accounts for 0.001-99.9% by weight, preferably 0.1-99% by weight, more preferably 1%-90% by weight, based on the total weight of the pharmaceutical composition.

In another preferred embodiment, the composition or medicament comprises: an oral preparation and a non-oral preparation.

In another preferred embodiment, the preparation comprises: a powder, a granule, a capsule, an injection, a tincture, an oral liquid, a tablet or a lozenge.

In another preferred embodiment, the composition is an oral preparation.

In another preferred embodiment, the composition (such as, the pharmaceutical composition) is administered to a mammal by oral, intravenous, or topical injection.

In another preferred embodiment, the mammal comprises a mammal having acquired immunodeficiency syndrome (AIDS).

In another preferred embodiment, the mammal comprises a human or a non-human mammal.

In another preferred embodiment, the non-human mammal comprises a rodent such as a mouse or a rat.

In the second aspect of the present invention, a compound of formula (II), or a pharmaceutically acceptable salt thereof is provided,

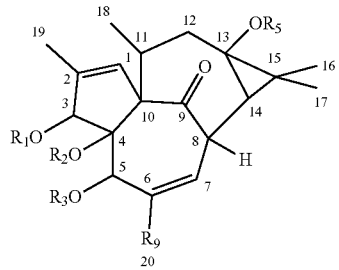

II wherein

R$_1$ is selected from H, or COCH(CH$_3$)CH(CH$_3$)$_2$ or substituted or unsubstituted OCC$_6$H$_5$;

R$_2$ is selected from H, or COCH(CH$_3$)CH(CH$_3$)$_2$ or substituted or unsubstituted OCC$_6$H$_5$;

R$_3$ is selected from H, or COCH(CH$_3$)CH(CH$_3$)$_2$ or substituted or unsubstituted OCC$_6$H$_5$;

R$_5$ is selected from H, COCH$_3$, OCH$_2$CH$_3$ or CO(CH$_2$)$_{10}$CH$_3$;

R$_9$ is selected from CH$_2$OR$_4$ or —C(O)R$_{10}$; wherein R$_4$ is selected from H, COCH$_3$, CH$_2$CH$_3$, OCH$_2$CH$_3$, CO(CH$_2$)$_{10}$CH$_3$ or CO(CH$_2$)$_{14}$CH$_3$; and R$_{10}$ is selected from the group consisting of: H, C$_1$-C$_6$ alkyl, C$_2$-C$_6$ alkenyl, C$_2$-C$_6$ alkynyl, C$_1$-C$_6$ alkoxy, —OH, C$_1$-C$_6$ ester group, and a combination thereof;

or, any one or two of R$_1$ and R$_2$, R$_2$ and R$_3$, R$_3$ and R$_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein the "substituted" means that H in a group is substituted with one or more substituents selected from the group consisting of: halogen, C$_1$-C$_6$ alkyl, C$_1$-C$_6$ haloalkyl, C$_2$-C$_6$ alkenyl, C$_2$-C$_6$ alkynyl.

provided that, R$_1$, R$_2$, R$_3$ and R$_4$ are not simultaneously H; and when R$_1$ is COCH(CH$_3$)CH(CH$_3$)$_2$ and both of R$_2$ and R$_3$ are H, R$_4$ is OCH$_2$CH$_3$, CO(CH$_2$)$_{10}$CH$_3$, or CO(CH$_2$)$_{14}$CH$_3$.

In another preferred embodiment, R$_2$ and R$_3$ form a 5-7 membered substituted or unsubstituted heterocycle with an adjacent ring carbon atom.

In another preferred embodiment, R$_2$ and R$_3$ form a 5-6 membered substituted or unsubstituted heterocycle with an adjacent ring carbon atom.

In another preferred embodiment, R$_2$ and R$_3$ form a 5-membered substituted or unsubstituted heterocycle with an adjacent ring carbon atom.

In another preferred embodiment, R$_1$ and R$_2$ form a 5-7 membered substituted or unsubstituted heterocycle with an adjacent ring carbon atom.

In another preferred embodiment, R$_1$ and R$_2$ form a 5-6 membered substituted or unsubstituted heterocycle with an adjacent ring carbon atom.

In another preferred embodiment, R$_1$ and R$_2$ form a 5-membered substituted or unsubstituted heterocycle with an adjacent ring carbon atom.

In another preferred embodiment, R$_3$ and R$_9$ form a 5-7 membered substituted or unsubstituted heterocycle with an adjacent ring carbon atom.

In another preferred embodiment, R$_3$ and R$_9$ form a 5-6 membered substituted or unsubstituted heterocycle with an adjacent ring carbon atom.

In another preferred embodiment, R$_3$ and R$_9$ form a 6-membered substituted or unsubstituted heterocycle with an adjacent ring carbon atom.

In another preferred embodiment, the heterocycle is a 5-6 membered heterocycle containing 2 oxygen atoms with 1-2 C$_1$-C$_3$ alkyl.

In another preferred embodiment, the heterocycle is selected from the group consisting of:

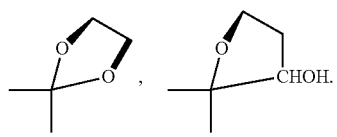

In another preferred embodiment, the "substituted" means that H in a group is substituted with one or more substituents selected from the group consisting of: halogen, C$_1$-C$_4$ alkyl, C$_1$-C$_4$ haloalkyl, C$_2$-C$_4$ alkenyl, C$_2$-C$_4$ alkynyl.

In another preferred embodiment, any one group of R$_1$ and R$_2$, R$_2$ and R$_3$, R$_3$ and R$_9$ respectively and independently forms a 5-7 membered substituted or unsubstituted heterocycle containing 2-3 oxygen atoms and 0-1 heteroatoms selected from N or S.

In another preferred embodiment, any two groups of R$_1$ and R$_2$, R$_2$ and R$_3$, R$_3$ and R$_9$ respectively and independently form a 5-7 membered substituted or unsubstituted heterocycle containing 2-3 oxygen atoms and 0-1 heteroatoms selected from N or S.

In another preferred embodiment, the halogen is selected from the group consisting of: F, Cl, Br and I.

In another preferred embodiment, the compound has a structure as shown in formula IIa or formula IIb:

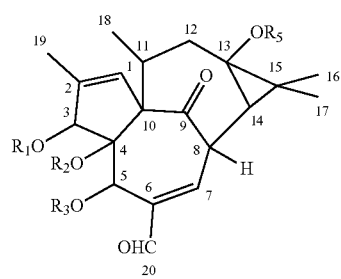

IIa

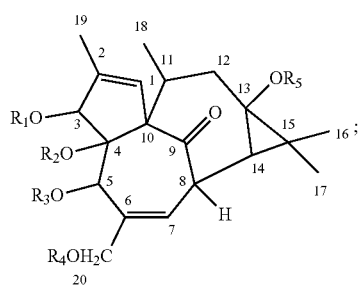

IIb and R$_1$, R$_2$, R$_3$, R$_4$ and R$_5$ are defined as formula II.

In another preferred embodiment, the compound is selected from the group consisting of:

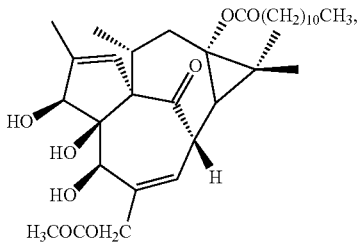

16A-12A

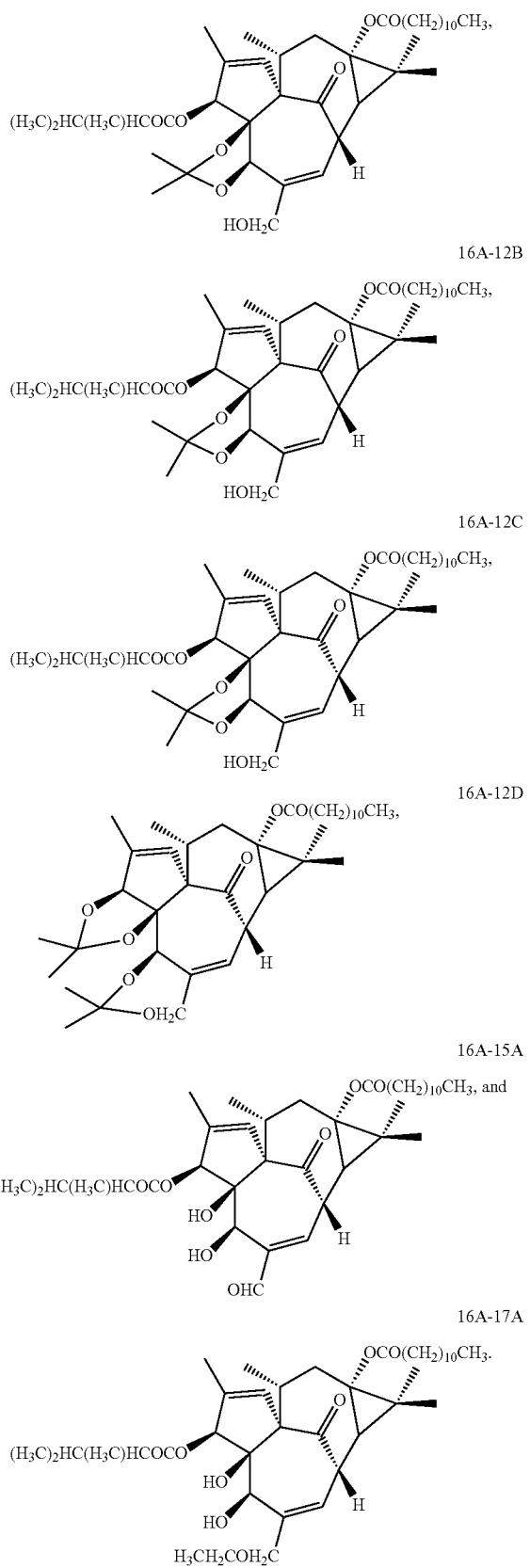

In the third aspect of the present invention, a pharmaceutical composition is provided, comprising:

(a1) a first active ingredient for interfering with the HIV virus latency, which is a compound of formula I or an acceptable salt thereof;

(a2) a second active ingredient for inhibiting replication of HIV virus, which is an antiretroviral drug; and (b) a pharmaceutically acceptable carrier;

wherein the compound of formula I is defined as described in the first aspect of the invention.

In another preferred embodiment, the compound of formula I has a structure as shown in formula II.

In another preferred embodiment, the antiretroviral drug is selected from the group consisting of: a reverse transcriptase inhibitor, a protease inhibitor, a co-receptor antagonist, a retroviral integrase inhibitor, a viral adsorption inhibitor, and a specific viral transcriptional inhibitor, a cyclin-dependent kinase inhibitor, an anti-HIV antibody, and a combination thereof.

In another preferred embodiment, the weight ratio of the first active ingredient to the second active ingredient is 0.1%-99%, preferably 20%-80%.

In another preferred embodiment, the pharmaceutical dosage form is an oral or a non-oral dosage form.

In another preferred embodiment, the oral dosage form is a tablet, a powder, a granule or capsule, or an emulsion or syrup.

In another preferred embodiment, the non-oral dosage form is an injection or a dosage form administrated by needle.

In another preferred embodiment, the concentration of the compound of formula I (or the compound of formula II) or a pharmaceutically acceptable salt thereof is 0.001 ug-1,000,000 ug/ml, preferably 0.01 ug-1000 ug/ml, more preferably, 0.1 ug-100 ug/ml.

In the fourth aspect of the present invention, an in vitro non-therapeutic method for inducing a HIV proviral expression in a latently infected cell of the HIV virus is provided, comprising the steps of: in the presence of the compound of formula I as defined in the first aspect of the present invention or the compound of formula II according to the second aspect of the present invention or a pharmaceutically acceptable salt thereof, culturing cells latently infected by HIV virus to cause the expression of the latent HIV provirus, thereby activating the latent HIV virus.

In another preferred embodiment, the method further comprises killing or inhibiting the activated HIV virus.

In the fifth aspect of the present invention, a non-therapeutic method for activating a latent HIV virus is provided, comprising the steps of: administering to a subject in need thereof the compound of formula I as defined in the first aspect of the present invention or the compound of formula II according to the second aspect of the present invention or a pharmaceutically acceptable salt thereof is provided, thereby activating the latent HIV virus.

In the sixth aspect of the present invention, a method of preparing a pharmaceutical composition for treating AIDS is provided, comprising the steps of: mixing the compound of formula I as defined in the first aspect of the present invention or the compound of formula II according to the second aspect of the present invention or a pharmaceutically acceptable salt thereof with a pharmaceutically acceptable carrier, thereby forming a pharmaceutical composition.

In another preferred embodiment, a method of activating a latent HIV virus; and/or a method of treating AIDS is further provided by the present invention, administering to a subject in need thereof a safe and effective amount of the compound of formula I as defined in the first aspect of the present invention or the compound of formula II according to the second aspect of the present invention or an acceptable salt thereof, or a pharmaceutical composition according to the third aspect of the present invention.

In another preferred embodiment, the subject in need thereof is a mammal, such as a human.

In another preferred embodiment, the administered dose is 0.1-2000 mg per day, preferably 1-300 mg/day, for an adult.

In the seventh aspect of the present invention, a kit is provided, which comprises:

a formulation comprising the compound of formula I as defined in the first aspect of the present invention or the compound of formula II according to the second aspect of the present invention or a pharmaceutically acceptable salt thereof;

a formulation comprising an antiretroviral drug; and instructions.

In another preferred embodiment, the dosage forms of the formulation comprising the compound of formula I as defined in the first aspect of the present invention or the compound of formula II according to the second aspect of the present invention or a pharmaceutically acceptable salt thereof or the formulation comprising an antiretroviral drug include capsules, tablets, suppositories, or intravenous injections, respectively.

In another preferred embodiment, in the formulation comprising the compound of formula I as defined in the first aspect of the present invention or the compound of formula II according to the second aspect of the present invention or an acceptable salt thereof, the concentration of the compound of formula I as defined in the first aspect of the present invention or the compound of formula II according to the second aspect of the present invention or an acceptable salt thereof is 0.001 μg-1,000,000 μg/ml, preferably, 0.01 μg-1000 μg/ml.

In another preferred embodiment, the antiretroviral drug comprises a reverse transcriptase inhibitor, a protease inhibitor, a fusion inhibitor, an integrase inhibitor, or a combination thereof.

In another preferred embodiment, the following usage is described in the instructions:

(I) administering to a subject in need thereof a formulation comprising the formulation comprising the compound of formula I as defined in the first aspect of the present invention or the compound of formula II according to the second aspect of the present invention or an acceptable salt thereof;

(II) administering to the subject a formulation comprising an antiretroviral drug, 5-50 hours, preferably 10-48 hours, more preferably 15-24 hours after the step (I); and optionally (III) Repeating steps (I)-(II).

In the eighth aspect of the present invention, an in vitro non-therapeutic method for inhibiting and/or killing a latent HIV virus is provided, comprising the steps of:

(i) cultivating a cell latently infected by the HIV virus in the presence of the compound of formula I as defined in the first aspect of the present invention or the compound of formula II according to the second aspect of the present invention or a pharmaceutically acceptable salt thereof, thereby obtaining a cell containing an activated HIV virus;

(ii) adding an antiretroviral drug to the cell containing the activated HIV virus in (i), thereby inhibiting and/or HIV virus.

In another preferred embodiment, the incubation time in step (i) is 5-50 hours, preferably 10-48 hours, more preferably 15-24 hours.

In the ninth aspect of the present invention, a method of treating a latent infection of an HIV virus is provided, comprising the steps of:

(I) administering to a subject in need thereof a formulation comprising the compound of formula I as defined in the first aspect of the present invention or the compound of formula II according to the second aspect of the present invention or a pharmaceutically acceptable salt thereof;

(II) administering to the subject a formulation comprising an antiretroviral drug, 5-50 hours, preferably 10-48 hours, more preferably 15-24 hours after the step (I); and optionally, (III) repeating steps (I)-(II);

thereby treating the latent infection of HIV virus.

It should be understood that, within the scope of the present invention, each technical feature of the present invention described above and in the following (as examples) may be combined with each other to form a new or preferred technical solution, which is not listed here due to space limitations.

Figure 1:
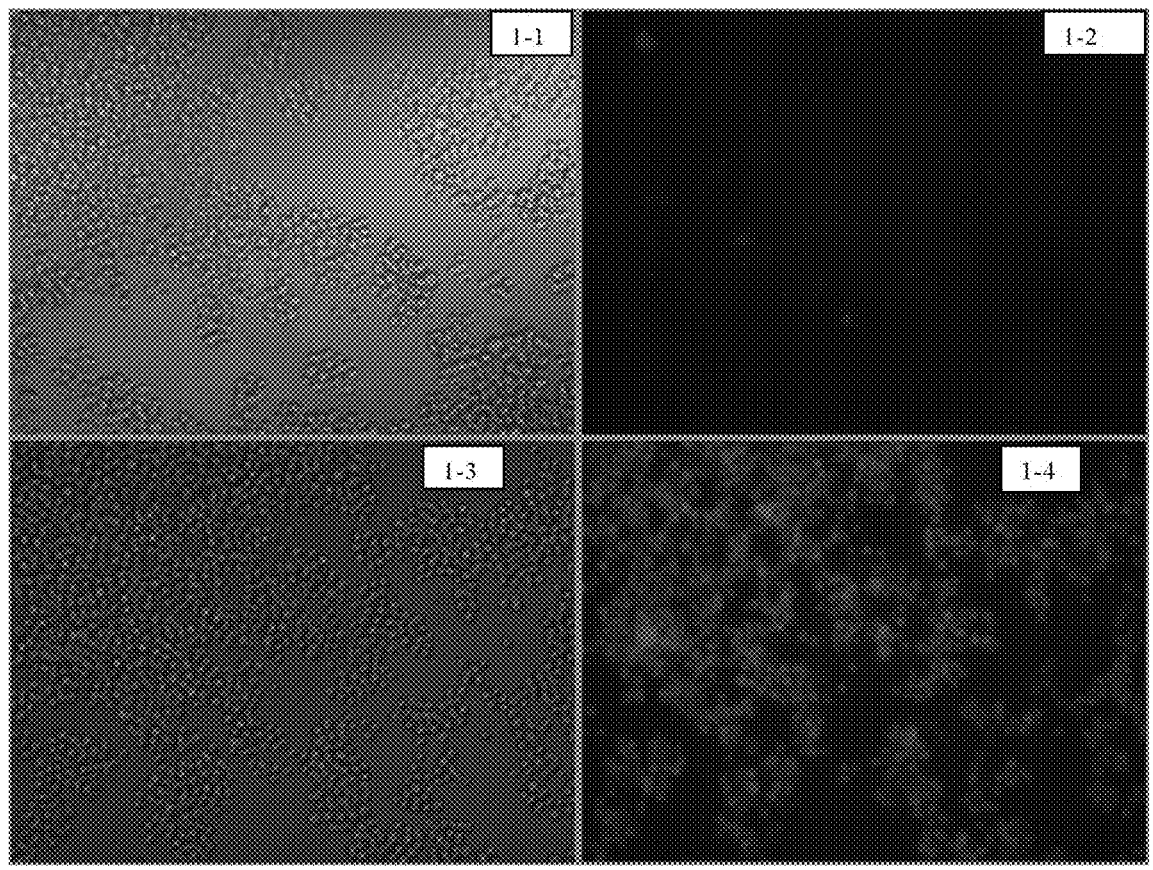
FIG. 1 shows the induction and activation of EK-16A (i.e., 16A) on HIV latency observed by the Fluorescence microscope.
Figure 2:
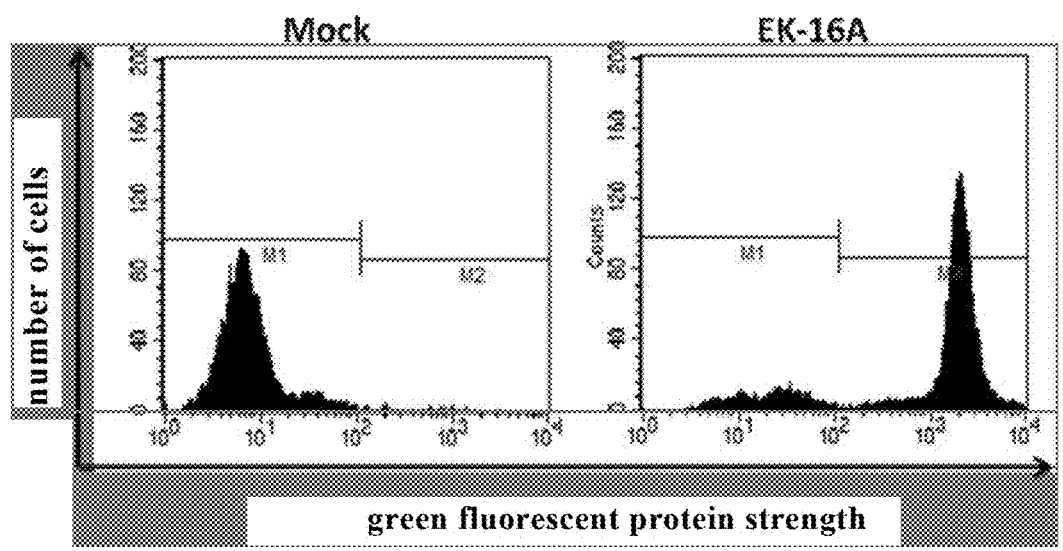
Figure 3:
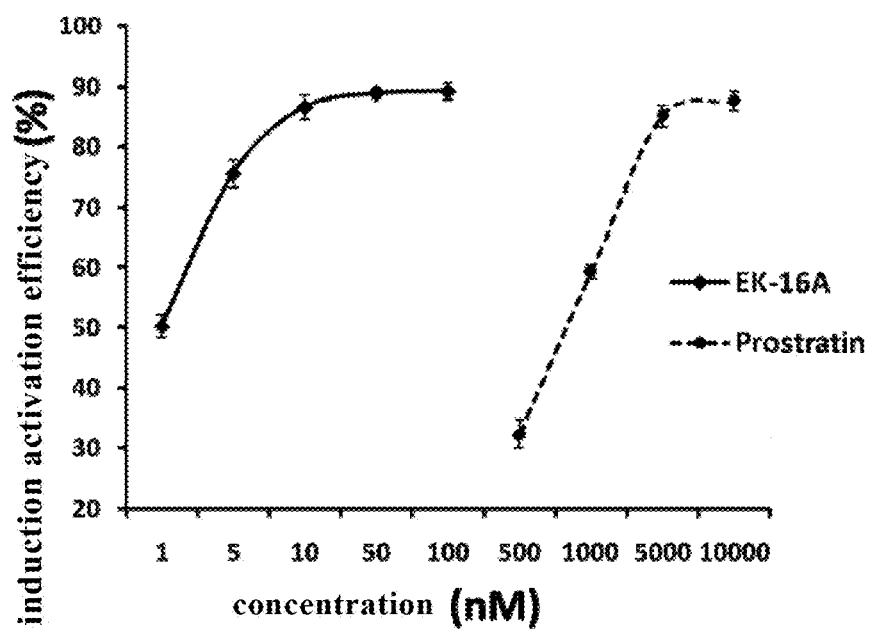

wherein, FIG. 1 specifically shows the expression of green fluorescence in cells after J-Lat-A10.6 cells are untreated or treated with 10 nM EK-16A for 48 h; unmedicated group (a white light photo is shown in FIG. 1-1, a fluorescence photo of the same field is shown in FIG. 1-2), EK-16A treatment group (a white light photo is shown in FIG. 1-3, a green fluorescence photo of the same field is shown in FIG. 1-4).

FIG. 2 shows the efficiency of induction and activation of EK-16A (i.e., 16A) on HIV latency detected by flow cytometry;

wherein FIG. 2 specifically shows the proportion of fluorescent cells obtained by flow cytometry analysis after J-Lat-A10.6 cells are untreated (MOCK group) or treated with 10 nM EK-16A for 48 h.

FIG. 3 shows a comparison of the activation efficiency of EK-16A (i.e., 16A) and the control drug Prostratin on the latent HIV in J-Lat-A10.6 cells;

wherein, the activation effect of different concentrations of EK-16A and Prostratin on the latent HIV in J-Lat-A10.6 cell line is detected by flow cytometry, and a concentration-dependent curve is drawn. All data results are the average of the data obtained from 3 independent experiments.

Figure 4:
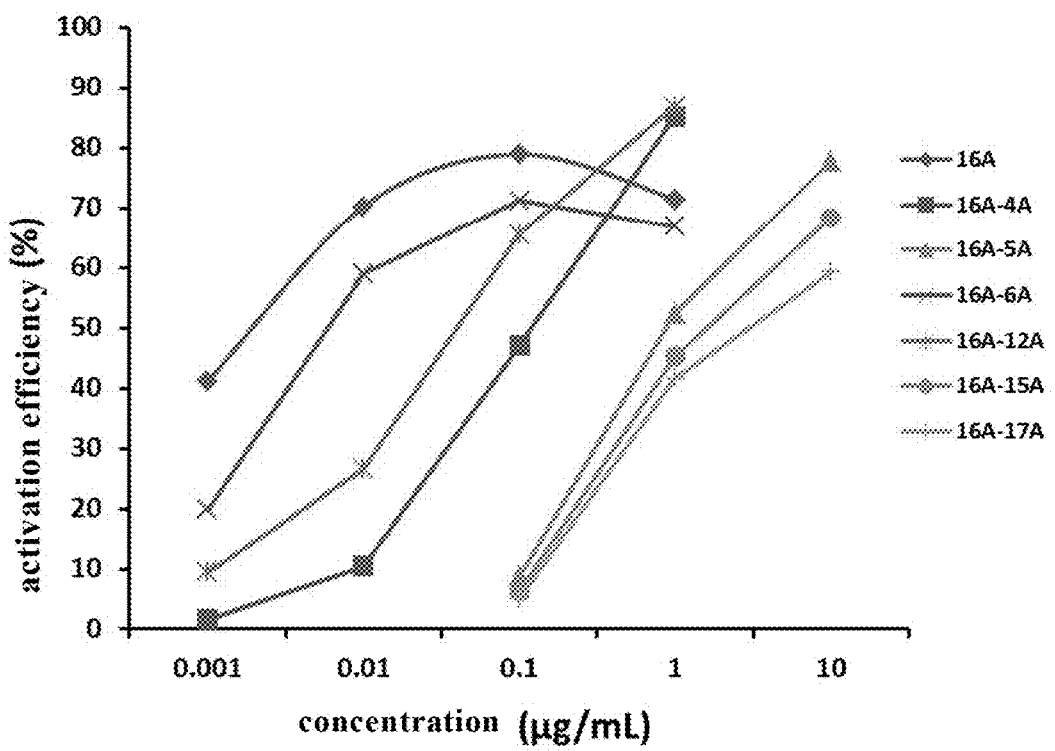

FIG. 4 shows the activation efficiency effect of the compounds in Examples 1-7 of the present invention on the latent HIV in C11 cells;

wherein, the activation effect of different concentrations of the compounds in Examples 1-7 on latent HIV in the C11 cell line is detected by flow cytometry, and a concentration-dependent curve is drawn. All data results are the average of the data obtained from 3 independent experiments.

Figure 5:
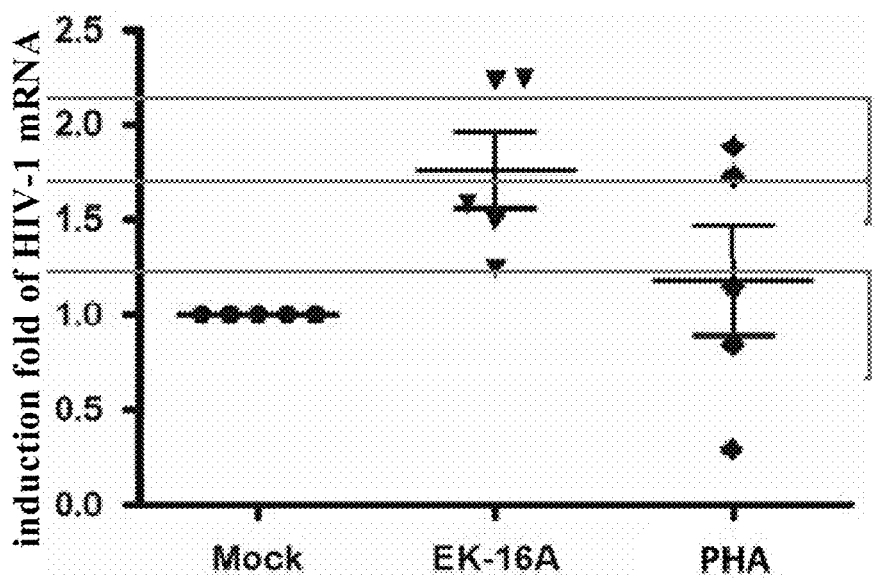

FIG. 5 shows the activation effect of EK-16A (i.e., 16A) and positive control PHA on resting blood CD4+ T cells in peripheral blood of AIDS patients.

DETAILED DESCRIPTION

After an extensive and in-depth study and through screening a large number of compounds, it was first discovered that the ingenol compounds and the derivatives thereof (the compounds of formula I and formula II) have the effect of anti-HIV latency. Specifically, the inventor used a unique active screening method to screen ou the ingenol compounds and the derivatives thereof (the compounds of formula I and formula II), and which can be used as a therapeutic drug for anti-AIDS. The ingenol compounds and derivatives thereof (compounds of formula I and formula II) of the present invention have the effect of interfering with HIV latency, and when used in combination with antiretroviral drugs, the activated latently infected cells can be removed, thereby accelerating the removal of the latent virus reservoir, providing a new way to cure AIDS completely. On this basis, the inventors complete the present invention.

Group Definition

As used herein, the term "substituted or unsubstituted" means that the group may be unsubstituted, or the H in the group is substituted with one or more (such as, 1-10, preferably 1-5, more preferably 1-3, most preferably 1-2) substituents.

As used herein, the "substitution" or "substituted" means that the group has one or more (preferably 1-6, more preferably 1-3) substituents selected from the group consisting of: halogen, $C_1$-$C_6$ alkyl, $C_1$-$C_6$ haloalkyl, $C_2$-$C_6$ alkenyl, $C_2$-$C_6$ alkynyl.

As used herein, the term "$C_1$-$C_6$ alkyl" refers to a straight or branched alkyl group having 1 to 6 carbon atoms, such as methyl, ethyl, propyl, isopropyl, butyl, isobutyl, sec-butyl, t-butyl, or the like. As used herein, the term "$C_2$-$C_6$ alkenyl" refers to a straight or branched alkenyl group having 2 to 6 carbon atoms, such as ethenyl, allyl, 1-propenyl, isopropenyl, 1-butenyl, 2-butenyl, or the like.

As used herein, the term "$C_2$-$C_6$ alkynyl" refers to a straight or branched alkynyl group having 2 to 6 carbon atoms, such as ethynyl, propynyl, or the like.

As used herein, the term "$C_1$-$C_6$ haloalkyl" refers to a straight or branched alkyl group having 1 to 6 carbon atoms in which hydrogen is substituted with one or more halogen, for example, halomethyl, haloethyl, halopropyl, haloisopropyl, or the like.

As used herein, the term "$C_1$-$C_6$ alkoxy" refers to a group having a "($C_1$-$C_6$ alkyl)-O-" structure, for example, $CH_3$—O—, $C_2H_5$—O—, $C_3H_7$—O—, or the like.

As used herein, the term "$C_1$-$C_6$ ester group" refers to a group having a ($C_1$-$C_6$ alkyl)-COO— structure, such as $CH_3COO$—, $C_2H_5COO$—, $C_3H_7COO$—, $(CH_3)_2CHCOO$—, $nC_4H_9COO$—, $tC_4H_9COO$—, or the like.

As used herein, the term "halogen" refers to fluorine, chlorine, bromine, or iodine, preferably fluorine and chlorine.

As used herein, the term "halogenated" refers to a group that is substituted with one or more of the same or different halogen atoms described as above, which may be partially halogenated or perhalogenated, such as trifluoromethyl, pentafluoroethyl, heptafluoroisopropyl, or the like.

The compounds of the present invention may contain one or more asymmetric centers and therefore occur as racemates, racemic mixtures, single enantiomers, diastereomeric compounds, and single diastereomers. The asymmetric center that can exist depends on the nature of the various substituents on the molecule. Each such asymmetric center will independently produce two optical isomers, and all possible optical isomers and diastereomeric mixtures and pure or partially pure compounds are included within the scope of this invention. The invention includes all isomeric forms of the compounds.

Active Ingredient

As used herein, the terms "active ingredient of the present invention", "ingenol compound and derivatives thereof of the present invention", "anti-HIV latent active ingredient of the present invention" and "formula I, formula II of the present invention" can be used interchangeably and refer to active ingredients extracted from the *Euphorbia kansui* and Euphoribia having the effect of inducing proviral expression of HIV latently infected cells to activate latent viruses.

In the present invention, the anti-HIV latent active ingredient can be extracted from the *Euphorbia kansui* as the raw material, and can be obtained by chemical synthesis.

In the present invention, the active ingredient of the present invention has the formula of Formula I:

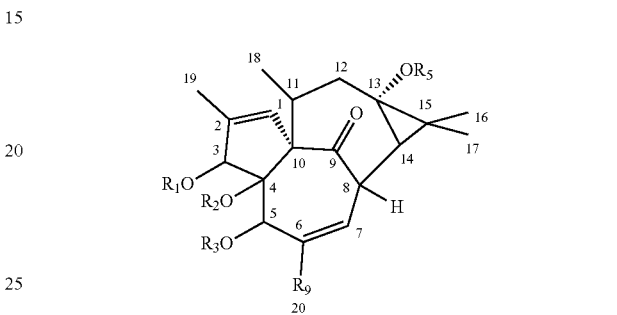

wherein $R_1$ is selected from H, substituted or unsubstituted $COCH(CH_3)CH(CH_3)_2$ or substituted or unsubstituted $OCC_6H_5$;

$R_2$ is selected from H, substituted or unsubstituted $COCH(CH_3)CH(CH_3)_2$ or substituted or unsubstituted $OCC_6H_5$;

$R_3$ is selected from H, substituted or unsubstituted $COCH(CH_3)CH(CH_3)_2$ or substituted or unsubstituted $OCC_6H_5$;

$R_5$ is selected from H, $COCH_3$, $OCH_2CH_3$ or $CO(CH_2)_{10}CH_3$;

$R_9$ is selected from the group consisting of: $CH_2OR_4$ and —$C(O)R_{10}$; wherein $R_4$ is selected from H, $COCH_3$, $OCH_2CH_3$, $CH_2CH_3$, or $CO(CH_2)_{10}CH_3$ or $CO(CH_2)_{14}CH_3$; $R_{10}$ is selected from the group consisting of: H, substituted or unsubstituted $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;

or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein the "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, $C_2$-$C_6$ alkynyl.

In a preferred embodiment, the compound has a structure as shown in formula Ic or formula Id:

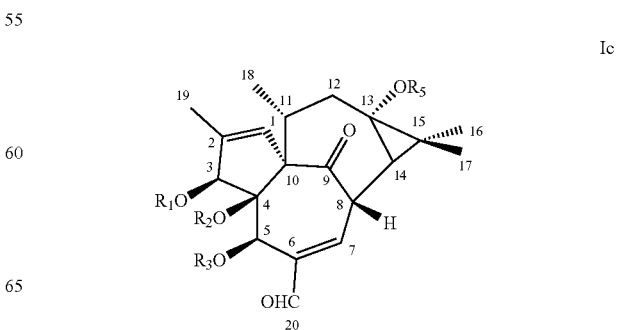

Ic

-continued

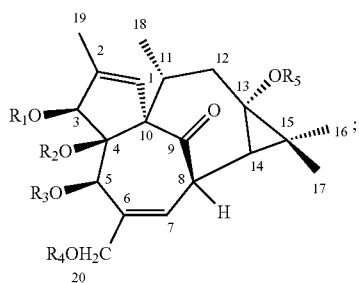

Id wherein $R_1$, $R_2$, $R_3$, $R_4$ and $R_5$ are defined as the first aspect of the present invention.

In the present invention, the active ingredient of the present invention has the formula of Formula II:

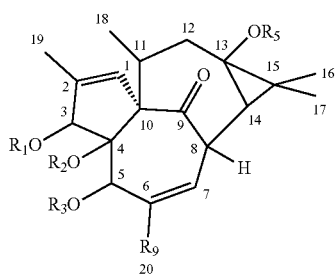

II wherein $R_1$ is selected from H, or $COCH(CH_3)CH(CH_3)_2$, or substituted or unsubstituted $OCC_6H_5$;

$R_2$ is selected from H, or $COCH(CH_3)CH(CH_3)_2$, or substituted or unsubstituted $OCC_6H_5$;

$R_3$ is selected from H, or $COCH(CH_3)CH(CH_3)_2$, or substituted or unsubstituted $OCC_6H_5$;

$R_5$ is selected from H, $COCH_3$, $OCH_2CH_3$, or $CO(CH_2)_{10}CH_3$;

$R_9$ is selected from $CH_2OR_4$ or $-C(O)R_{10}$; wherein $R_4$ is selected from H, $COCH_3$, $CH_2CH_3$, $OCH_2CH_3$, $CO(CH_2)_{10}CH_3$, or $CO(CH_2)_{14}CH_3$; and $R_{10}$ is selected from the group consisting of: H, $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;

or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, the heterocycle contains 2-3 oxygen atoms and 0-1 heteroatoms selected from N or S;

wherein the "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, $C_2$-$C_6$ alkynyl.

provided that, $R_1$, $R_2$, $R_3$ and $R_4$ are not simultaneously H; and when $R_1$ is $COCH(CH_3)CH(CH_3)_2$ and both of $R_2$ and $R_3$ are H, $R_4$ is $OCH_2CH_3$, $CO(CH_2)_{10}CH_3$ or $CO(CH_2)_{14}CH_3$.

In another preferred embodiment, the compound has a structure as shown in formula IIa or formula IIb:

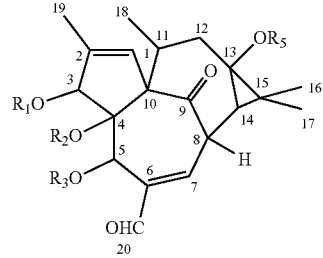

IIa

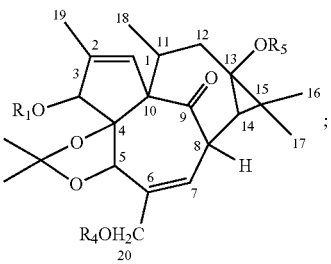

IIb wherein $R_1$, $R_2$, $R_3$, $R_4$ and $R_5$ are defined as formula II.

In another preferred embodiment, the compound is selected from the group consisting of:

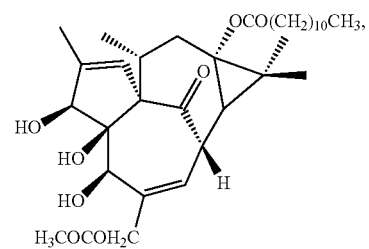

16A-12A

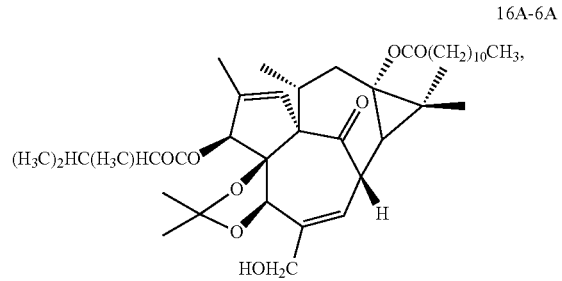

16A-6A

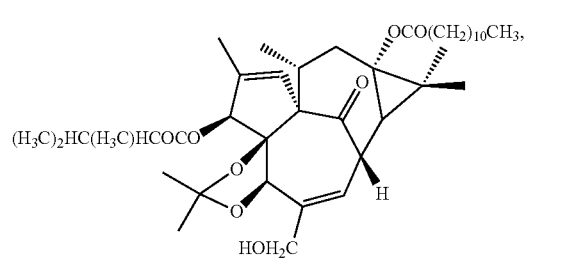

16A-12B

-continued

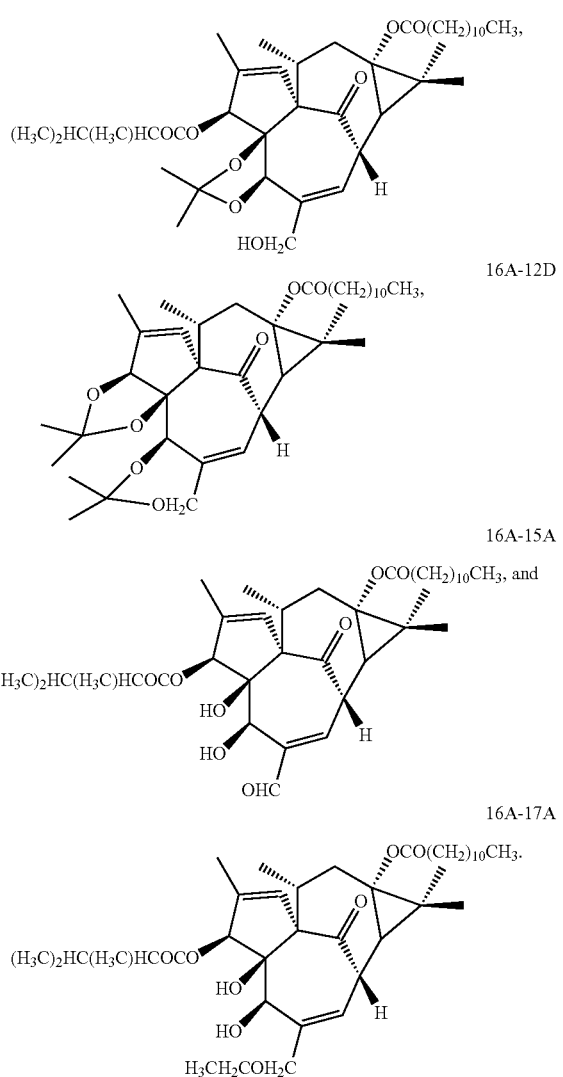

Activity Screening Assay

The present invention adopts the HIV latent cell model for the activity screening assay, and the results show that the ingenol compounds and derivatives thereof of the formula I and the formula II have anti-HIV latent effects, and according to the conventional method, the applicable dosage form is prepared for the anti-HIV latent effect assay. It is confirmed that the ingenol compound represented by the formula I and the formula II can cause the expression of HIV latent in infected cells, and has an effect of interfering with HIV latency, and when used in combination with antiretroviral drugs, the latently infected cells that are activated can be removed, thereby accelerating the removal of latent virus reservoirs.

The HIV latent cell model of the present invention comprises: a human T cell 10.6 clone strain carrying a green fluorescent protein gene (J-Lat-A10.6), which is provided by the National Institute of Health Research AIDS Reference Reagent Planning Department, established by Dr. Eric Verdin of the University of California.

The cells are small and the spherical cells are cultured in suspension. Human T cell Jurkat sperm cells are transfected by the retroviral vector carrying the green fluorescent protein gene HIV-R7/E-/GFP and sorted (Jordan A, Bisgrove D, Verdin E. HIV reproducibly establishes a latent infection after acute infection EMBO J 22:1868-1877, 2003); another established HIV latent screening model C11 clone is obtained by the twice of the sorting and activation on HIV lentivirus-infected T cells. (Chinese patent: 200810038851. X).

Composition and Method of Administration

As used herein, the term "composition" comprises (a) a composition for treating and/or preventing AIDS, (b) a composition for activating a latent HIV virus; in addition, the composition comprises a pharmaceutical composition, a food composition or a health care product composition.

The anti-HIV latent active ingredient of the present invention has an effect of interfering with HIV latency. Therefore, when an anti-HIV latent active ingredient of the invention is therapeutically administered or administered, the expression of a latent HIV virus can be promoted, thereby activating the latent HIV virus. In general, the active ingredients of the present invention may be formulated in a non-toxic, inert, and pharmaceutically acceptable carrier medium. The formulated pharmaceutical compositions can be administered by conventional routes including, but are not limited to, oral, intramuscular, intraperitoneal, intravenous, subcutaneous, intradermal, or topical administration.

The invention further provides a pharmaceutical composition comprising a safe and effective amount of an active ingredient of the present invention and a pharmaceutically acceptable carrier or excipient. Such carriers include, but are not limited to, saline, buffer, dextrose, water, glycerol, ethanol, and a combination thereof. The pharmaceutical preparation should be matched to the mode of administration. The pharmaceutical composition of the present invention can be prepared in the form of an injection, for example, by a conventional method using physiological saline or an aqueous solution containing glucose and other adjuvants. Pharmaceutical compositions such as tablets and capsules can be prepared by conventional methods. Pharmaceutical compositions such as injections, solutions, tablets and capsules are preferably produced under sterile conditions. The active ingredient is administered in a therapeutically effective amount, for example, about 1 microgram to 10 milligrams per kilogram of body weight per day. Preferably, the amount of glycyrrhizin or a derivative thereof may be from 0.1 to 2000 mg, preferably 1 to 300 mg/day, per day for an adult.

As a preventive and anti-AIDS drug, it can be made into oral and non-oral preparations. Oral administration can be prepared into tablets, powders, granules, capsules and the like, and the excipients used may be one or more of starch, lactose, sucrose, mannose, hydroxymethylcellulose, and the like. The disintegrant may be one or more of potato starch, hydroxymethylcellulose, and the like. The binding agent may be one or more of gum arabic, corn starch, gelatin, dextrin, and the like. The oral preparation may be further formulated into an emulsion, a syrup and the like in addition to the above dosage forms.

The non-oral preparation can be prepared as an injection, and can be prepared into injection using water for injection, physiological saline or dextrose water, or a certain proportion of ethanol, propanol or ethylene glycol may be added thereto.

Furthermore, the active ingredients of the present invention are also particularly suitable for use in combination with other anti-HIV drugs. In particular, the active ingredient of the present invention can be used in combination with an anti-retroviral drug to remove latently infected cells for the treatment of AIDS.

A further object of the present invention is to provide a method for preparing a drug for treating AIDS, which comprises: using the ingenol compound represented by the formula I and the formula II and a derivative thereof as a pharmaceutical raw material, and using the corresponding excipient, formulating into oral and non-oral preparations according to the conventional method, wherein the ingenol compound represented by the formula I and the formula II and derivatives thereof can be used in an amount of 0.1 to 2000 mg, preferably 1 to 300 mg/day, per day for an adult, and 1 to 5 times a day; and the amount and frequency of children should be reduced as appropriate on an adult basis.

Kit

The present invention also provides a kit (or the drug for interfering with HIV virus latency according to the first aspect of the present invention), which comprises:

a formulation comprising the ingenol compound represented by formula I or formula II and derivatives thereof;

a formulation comprising an antiretroviral drug; and instructions.

The preparation comprising the ingenol compound represented by Formula I or Formula II and a derivative thereof may be a unit dosage form containing an ingenol compound and a derivative thereof, and the preparation comprising the antiretroviral drug may be a unit dosage form containing an antiretroviral drug.

The kit contains at least two unit dosage forms containing an ingenol compound and a derivative thereof and a unit dosage form containing an antiretroviral drug; and preferably, each is 4-10.

As used herein, the term "unit dosage form" refers to a dosage form required to prepare a composition for single administration for ease of administration, including, but is not limited to various solid agents (such as, tablets), liquids, capsules, sustained release agents.

The following usage is described in the instructions of the kit of the present invention:

(I) administering to a subject in need thereof a formulation comprising the ingenol compound and derivatives thereof;

(II) administering to the subject a formulation comprising an antiretroviral drug, 5-50 hours, preferably 10-48 hours, more preferably 15-24 hours after the step (I); and optionally (III) Repeating steps (I)-(II).

Further, the antiretroviral drug which can be used in the kit of the present invention may be one or more, preferably, the antiretroviral drug may be various, and more preferably, it may be a pharmaceutical combination of antiretroviral cocktail therapies well known to those skilled in the art.

Method of Activating and Suppressing the Latent HIV Virus

The present invention also provides an in vitro non-therapeutic and in vivo therapeutic method of activating and suppressing a latent HIV virus.

Wherein, the in vitro non-therapeutic method of activating and suppressing a latent HIV virus (or inducing the HIV proviral expression in latently infected cells of HIV virus) comprises the steps of:

In the presence of the ingenol compound and derivatives thereof of the present invention, culturing the latently infected cells of HIV virus, thereby activating the latent HIV virus.

When an antiretroviral drug is further added to the culture system in which the latent HIV virus is activated after this step, the method of inhibiting and/or killing the latent HIV virus of the present invention is achieved.

A suitable in vivo treatment comprises the following steps:

(I) administering to a subject in need thereof a formulation comprising the ingenol compound and a derivative thereof of the present invention;

(II) administering to the subject a formulation comprising an antiretroviral drug, 5-50 hours, preferably 10-48 hours, more preferably 15-24 hours after the step (I); and optionally, (III) Repeating steps (I)-(II).

The Main Advantages of the Invention Include:

1. After extensive screening, a derivative of an ingenol compound capable of significantly interfering with the latent effects of HIV is first discovered.

2. A new use of an ingenol compound is provided and HIV latent in infected cells can be significantly expressed by the ingenol compound at low concentrations.

3. The ingenol compound and the derivative thereof can be used as an active ingredient to prepare a drug against HIV latency.

4. Further preparation of drugs for treating AIDS will provide a new way for the complete cure of AIDS.

The present invention is further described below with reference to specific embodiments. It should be understood that these examples are only for illustrating the present invention and not intended to limit the scope of the present invention.

The conditions of the experimental methods not specifically indicated in the following examples are usually in accordance with conventional conditions as described in Sambrook et al., Molecular Cloning: A Laboratory Manual (N.Y.: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise indicated, percentages and parts are by weight and parts by weight.

EXAMPLE 1

Preparation of the Ingenol Compound EK-16A (i.e., 16A) of the Present Invention

30 Kg of *E. kansui* roots and rhizomes were reflux-extracted twice with 8 times the amount of 95% ethanol for 2 hours respectively, and the resulting extract was recovered until an alcohol-free taste to obtain a concrete. The concrete was diluted with water to 3000 mL, and extracted for three times with an equal volume of dichloromethane, and the dichloromethane solvent was recovered to give 101.2 g of dichloromethane extract.

The conditions of the silica gel column chromatography were as follows: the mobile phase used was a petroleum ether-ethyl acetate solution having a volume ratio of 10-2:1. The conditions of the reverse phase chromatography purification were as follows: the filler used was octadecylsilyl silica gel, and the mobile phase used was a methanol-water solution having a volume ratio of 93% for socratic elution to give a compound EK-16A (360 mg) as light yellow viscous solid with UV absorption of 208 nm in 30 minutes.

The separation and purification comprised: the extract solution was concentrated and subjected to silica gel column chromatography and thin layer detection to obtain the desired fractions, which were purified by reverse phase chromatography to give 360 mg of compound EK-16A (i.e., 16A).

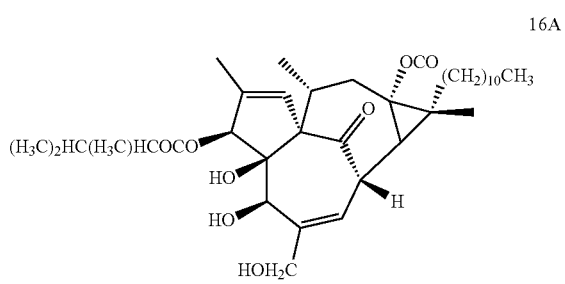

16A

1H NMR (CDCl3): 6.02 (m 1H H-1), 6.02 (m 1H H-7), 5.43 (m 1H H-3), 4.15 (s 2H H-20), 4.07 (dd 1H H-8), 4.05 (s 1H H-5), 3.58 (s 1H 4-OH), 2.71 (dd 1H H-12), 2.61 (m 1H H-11), 1.78 (s 3H Me-19), 1.19 (s 3H Me-17), 1.05 (s 3H Me-16), 0.96 (d 3H Me-18), 3-R (2.32 m 1H; 1.91 m 1H; 0.92 d 3H; 0.95 d 3H; 1.13 d 3H), 13-R (2.18 t 2H; 1.55 m 2H; 1.25 s —(CH2)8-; 0.87 t 3H).

EXAMPLE 2

Preparation of a Derivative 16A-4A of the Ingenol Compound of the Present Invention 3-O-(2,3-dimethylbutanoyl)-13-O-dodecanoyl ingenol (30 mg, 0.046 mmol) was dissolved in 5% KOH in MeOH (3 mL). After stirring at room temperature for 3 h, (DCM/MeOH=30/1, Rf of starting material was 0.5, which was developed as black by sulfuric acid ethanol, and Rf of product was 0.2, which was developed as black by sulfuric acid ethanol). TLC showed the complete reaction of the raw materials. For the extraction reaction system with ethyl acetate and water, the organic layer was washed with water, a saturated aqueous solution of sodium bicarbonate and brine and dried over anhydrous sodium sulfate. The filtrate was concentrated under reduced pressure to give 20 mg of a pale yellow viscous material. The filtrate was concentrated under reduced pressure and separated by silica gel column chromatography (DCM/MeOH=50/1), and then was purified by reverse phase preparative liquid phase and eluted with isocratic methanol/85% of water to give a compound 16A-4A (13 mg) as a pale yellow viscous solid in 37 minutes, with UV absorption of 206 nm.

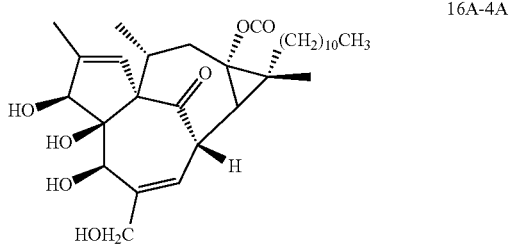

16A-4A

1H NMR (CDCl3): 6.03 (d 1H H-7), 5.93 (dd 1H H-1), 4.43 (s 1H H-3), 4.16 (ABq 1H H-20), 4.16 (ABq 1H H-20), 4.12 (s (OH) 1H), 4.06 (1H H-8), 3.82 (s 1H H-5), 3.33 (br(OH) 1H 5-OH), 3.35 (br(OH) 1H 4-OH), 2.72 (dd 1H), 2.43 (m 1H H-11), 2.24 (dd 1H H-12), 1.86 (d 3H Me-19), 1.22 (s, 3H, Me-17), 1.14 (d 1H H-14), 1.07 (s 3H Me-16), 0.92 (d 3H Me-18), 2.20 (t 2H), 1.55 (m 2H), 1.25 (s —(CH2)8-), 0.88 (t 3H), 3.67 (s(OH) 1H).

EXAMPLE 3

Preparation of a Derivative 16A-5A of the Ingenol Compound of the Present Invention The compound 16A (40 mg, 0.04 mmol) was dissolved in dichloromethane (5 ml), triethylamine was added, and a solution of acetyl chloride (0.05 ml) in dichloromethane was added dropwise under an ice bath, and the mixture was stirred at room temperature for 0.5 h. The reaction was monitored by TLC, in which using DCM/MeOH=80/1, the Rf of starting material was 0.4, which was developed as black by sulfuric acid ethanol, the Rf of product was 0.7, which was developed as black by sulfuric acid ethanol, and the reaction was completed after the disappearance of the material point. An ice water mixture (10 ml) was poured into a flask to quench the reaction and extracted with dichloromethane (3×10 ml). The organic phase was combined, and the organic phase was washed with NaHCO$_3$, anhydrous Na$_2$SO$_4$ and dried. The filtrate was concentrated under reduced pressure and separated by silica gel column chromatography (DCM/MeOH=50/1) to give compound 16A-5A, i.e., a yellow oily compound.

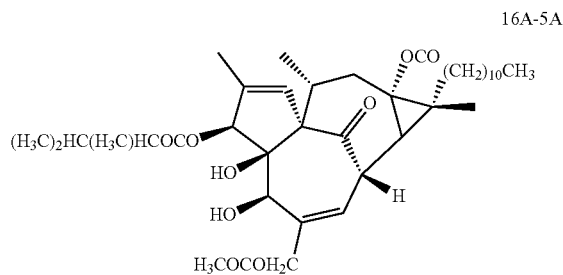

16A-5A

1H NMR (CDCl3): 6.10 (d 1H H-7), 6.02 (d 1H H-1), 5.45 (s 1H H-3), 4.75 (d 1H H-20), 4.48 (d 1H H-20), 4.05 (dd 1H H-8), 3.89 (d 1H −5), 3.55 (d 1H 4-OH), 3.50 (s 1H 5-OH), 2.58 (m 1H H-11), 2.06 (s 3H 20R), 1.79 (d 3H Me-19), 1.43 (m 1H H-14), 1.19 (s 3H Me-17), 1.07 (d 3H Me-16), 0.98 (d 3H Me-18), 3-R (2.32 m 1H; 1.92 m 1H; 0.92 d 3H; 0.97 d 3H; 1.14 d 3H), 13-R (2.20 t 2H; 1.56 m 2H; 1.25 s-(CH2)8-; 0.88 t 3H).

EXAMPLE 4

Preparation of a Derivative 16A-6A of the Ingenol Compound of the Present Invention 16A-4A was dissolved in dichloromethane (10 ml), triethylamine was added, and a solution of acetyl chloride (0.05 ml) in dichloromethane was added dropwise under an ice bath, and the mixture was stirred at room temperature for 0.5 h. The reaction was monitored by TLC, in which using DCM/MeOH=80/1, the Rf of raw material was 0.4, which was developed as black by sulfuric acid ethanol, the Rf1 of product was 0.7, which was developed as black by sulfuric acid ethanol, and the reaction was completed after the disappearance of the material point. An ice-water mixture (10 ml) was poured into a flask to quench the reaction and extracted with acetic ether (3×10 ml). The organic phase was combined, and the organic phase was washed with NaHCO₃, anhydrous Na₂SO₄, and dried, and the filtrate was concentrated under reduced pressure and separated by silica gel column chromatography (DCM/MeOH=80/1) to give compound 16A-6A, i.e., an orange-red oily compound.

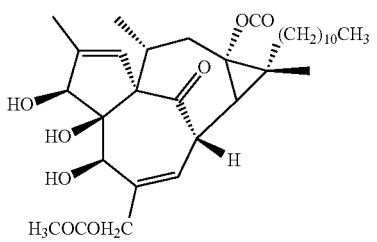

16A-6A

1H NMR (CDCl3): 6.09 (dd 1H H-7), 5.93 (dd 1H H-1), 4.71 (d 1H H-20), 4.52 (d 1H H-20), 4.45 (dd 1H H-5), 4.01 (dd 1H H-8), 3.70 (d 1H 4-OH), 2.72 (dd 1H H-12), 2.25 (d 1H H-12), 2.06 (s 3H 20R), 1.86 (dd 3H Me-19), 1.77 (m 1H H-14), 1.22 (s 3H Me-17), 1.07 (s 3H Me-16), 0.97 (d 3H M-18), 2.20 (t 2H; 1.55 m 2H; 1.25 s —(CH2)8-; 0.88 t 3H).

EXAMPLE 5

Preparation of a Derivative 16A-12A of the Ingenol Compound of the Present Invention Compound 16A (60 mg, 0.046 mmol) was dissolved in acetone (6 ml), concentrated sulfuric acid (60 ul) was slowly added dropwise, and the mixture was stirred at room temperature overnight (DCM/MeOH=50/1, Rf of starting material was 0.2, and Rf1 of product 1 was 0.8). TLC showed that the starting material was completely reacted. The reaction was quenched by slowly dropwise adding NaHCO₃ to the reaction mixture. The reaction system was extracted with dichloromethane, and the organic layer was washed with water, saturated aqueous NaHCO₃ and brine, and dried over anhydrous sodium sulfate. The filtrate was concentrated under reduced pressure to give an oily compound, compounds obtained and separated by silica gel column chromatography (DCM/MeOH=80/1) were combined, which was purified by reverse phase preparative liquid phase and eluted with isocratic methanol/95% water to give compound 16A-12A (2.3 mg) as a pale yellow viscous solid in 24 minutes, with a UV absorption of 235 nm.

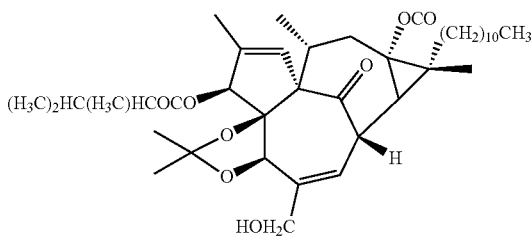

16A-12A

1H NMR (CDCl3): 6.15 (d J=5.1 1H H-1), 5.99 (d J=5.1 1H H-7), 5.33 (s 1H H-3), 4.34 (s 1H H-5), 4.12 (dd 1H H-8), 2.80 (m 1H H-11), 2.67 (dd J=3.2, 13.4 1H H-12a), 2.35 (m 1H C-2'), 2.31 (dd J=5.5, 11.5 1H H-12b), 2.20 (t J=7.5 2H C-2"), 1.92 (m 1H C-3'), 1.79 (d J=1.5 3H Me-19), 1.55 (m 2H C-11"), 1.23 (s 3H Me-17), 1.10 (d J=6.9 3H C-5'), 1.08 (s 3H Me-16), 1.00 (d J=6.9 3H C-6'), 0.93 (d J=6.9 3H C-4'), 0.90 (d J=7.2 3H Me-18), 0.88 (t J=7.2 3H C-12"), 1.25 (s —(CH2)8)-, 1.35 (s 3H), 1.48 (s 3H).

13C NMR (CDCl3): 127.7 (C-1), 132.2 (C-2), 82.6 (C-3), 83.1 (C-4), 70.9 (C-5), 138.8 (C-6), 43.9 (C-8), 205.9 (C-9), 92.3 (C-10), 38.3 (C-11), 35.7 (C12), 70.0 (C-13), 29.7 (C14), 31.7 (C-15), 23.5 (C-16), 17.8 (C-17), 18.7 (C-18), 16.8 (C-19), 66.9 (C20), 177.0 (C-1'), 46.7 (C-2'), 31.7 (C-3'), 21.4 (C-4'), 20.0 (C-5'), 15.0 (C-'), 175.0 (C-1"), 35.3 (C-2"), 28.8 (C-3"), 30.6 (C-4"), 30.5 (C-5"), 30.3 (C-6"), 30.2 (C-7"), 30.1 (C-8"), 30.1 (C-9"), 32.8 (C-10"), 23.6 (C-11"), 14.2 (C-12"), 111.9 (C-1'''), 28.6 (C-2'''), 52.57 (C-2''')

EXAMPLE 6

Preparation of a Derivative 16A-15A of the Ingenol Compound of the Present Invention Potassium peroxymonosulfate (oxone) (47.6 mg, 77.5 mmol), tetramethylpiperidine (tempo) (0.12 mg, 0.8 mmol), CaCl₂ (0.86 mg, 7 8 mmol) were added to a solution of 16A (50 mg, 77.5 mmol) in DCM. After the mixture was stirred at room temperature for 2 h, the starting material was completely reacted by TLC monitoring. Using DCM/MeOH=80/1, two newly formed dots were found, in which Rf of raw material was 0.2, Rf1 of product was 0.4, and Rf2 of product was 0.8. The inorganic salt was removed by filtration and the organic phase was concentrated, which was purified by reverse phase preparative liquid phase and eluted with isocratic methanol/95% water to give compound 16A-15A (1.8 mg) as a light yellow viscous solid, with a UV absorption of 226 nm.

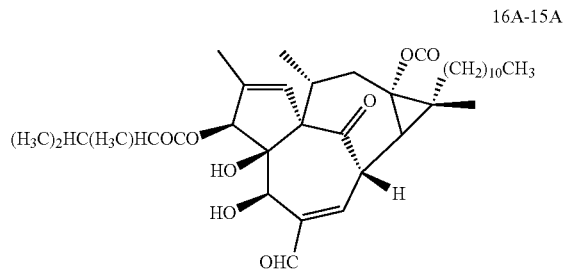

16A-15A

1H NMR (CDCl3): 9.34 (s 1H H-20), 6.50 (s 1H H-7), 6.14 (s 1H H-1), 5.25 (s 1H H-3), 4.29 (d 1H H-8), 3.57 (s 1H 5-OH), 3.57 (s 1H 4-OH), 3.89 (t 1H H-5), 2.72 (dd 1H H-12), 2.39 (dd 1H H-12), 2.44 (m 1H H-11), 1.79 (s 3H Me-19), 1.28 (s 3H Me-17), 1.20 (d 1H H-14), 1.09 (s 3H Me-16), 1.01 (d 3H Me-18), 3-R (2.35 m 1H; 1.93 m 1H; 0.94 d 3H; 0.97 d 3H; 1.16 d 3H), 13-R (2.21 t 2H; 1.55 m 2H; 1.25 s —(CH2)8-; 0.88 t 3H).

EXAMPLE 7

Preparation of a Derivative 16A-17A of the Ingenol Compound of the Present Invention Ethyl bromide (10 mg, 93 mmol), potassium carbonate (16 mg, 116.25 mmol) were added to a solution of 16A (50 mg, 77.5 mmol) in acetonitrile solution. After the mixture was stirred at 70° C. overnight, the starting material was completely reacted by TLC monitoring. Using DCM/

MeOH=60/1, a newly formed dot was found, in which Rf of raw material was 0.3, and Rf of product was 0.25. The organic solvent was removed and dried under reduced pressure, and after adding a small amount of water, the mixture was extracted with ethyl acetate. The organic phase was washed with saturated brine, dried over anhydrous sodium sulfate and concentrated. Reversed phase preparative liquid phase was performed for purification, and isocratic methanol/90% water was used in elution to give compound 16A-17A (3.8 mg) as a pale yellow viscous solid, with a UV absorption of 226 nm.

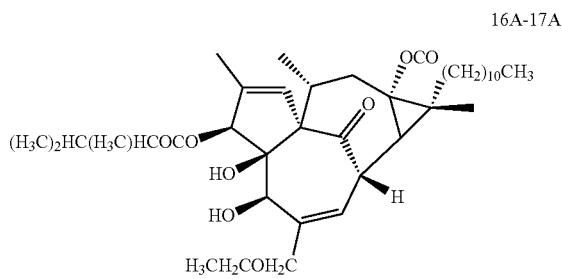

16A-17A

1H NMR (CDCl3): 6.20 (s 1H H-7), 5.51 (s 1H H-1), 5.33 (s 1H H-3), 4.79 (s 1H H-5), 4.18 (s 1H H-8), 2.67 (dd 1H H-12), 2.35 (m 1H H-11), 1.88 (s 3H Me-19), 1.80 (s 2H H-20), 1.35 (s 3H Me-17), 1.12 (s 3H Me-16), 0.84 (d 3H Me-18), 13-R (2.20 t 2H; 1.55 m 2H; 1.25 s —(CH2)8; 0.88 t 3H)0

EXAMPLE 8

The Ingenol Compounds and the Derivatives Thereof of the Present Invention can High Efficiently Activate HIV Expression in Latent Cells J-Lat-A10.6 or C11 cells were seeded in 96-well plates at 2×10E4 cells per well, and 100 μl of 1640 medium (Gibco) containing 10% FBS (Gibco) was added to each well. After the cells were treated with the compounds in Examples 1-7 for 48 h, the green fluorescence expression of the cells was observed under a fluorescence microscope, the cells were collected for flow cytometry detection, and the proportion of fluorescent cells was analyzed.

The results were shown in FIGS. 1 and 2. The results showed that in HIV-infected cells that were not treated with an inducer, the proportion of cells positive for fluorescence was only about 1-2% background activation (FIG. 1-1 and FIG. 1-2). After treatment with 10 nM EK-16A (i.e., 16A), the proportion of cells expressing green fluorescence in the cell model was significantly increased; wherein, the proportion of green fluorescent positive cells in J-Lat-A10.6 cells treated with the compound of Example 1 was as high as 90% (FIG. 1-3, FIG. 1-4, FIG. 2), and the proportion of green fluorescent positive cells in C11 cells was also nearly 80%.

The activity data after the treatment of the compounds in Examples 1-7 were shown in Table 1.

TABLE 1

| | $EC_{50}$ | activation rate |
|---|---|---|
| control group (not treated with the compounds in Examples 1-7) | no | 2% |

TABLE 1-continued

| | $EC_{50}$ | activation rate |
|---|---|---|
| Example 1 | 0.0026 μg/ml | 93% |
| Example 2 | 0.08 μg/ml | 89% |
| Example 3 | 0.09 μg/ml | 81% |
| Example 4 | 0.007 μg/ml | 72% |
| Example 5 | 0.05 μg/ml | 90% |
| Example 6 | 1.1 μg/ml | 73% |
| Example 7 | 1.18 μg/ml | 64% |

The results showed that the activation rate of HIV virus was increased by 32-45 times after the treatment of Examples 1-7 compound compared with the control group.

The results showed that the ingenol compounds and their derivatives had efficient activation effects on latent viruses in HIV latently infected cells.

EXAMPLE 9

Comparison of the Activation Efficiency of the Ingenol Compounds and Their Derivatives and PKC Activator Prostratin on the Latent HIV-1

J-Lat-A10.6 or C11 cells were seeded in 96-well plates at 2×10E4 cells per well, and 100 μl of 1640 medium (Gibco) containing 10% FBS (Gibco) was added to each well. After treatment with different concentrations of compounds (such as the compounds in Examples 1-7) and Prostratin for 48 h, the cells were collected for flow cytometry detection and the proportion of fluorescent cells was analyzed.

The results were shown in FIGS. 3 and 4.

The results showed that a better activation concentration of the ingenol compound and the derivatives thereof ranged from 1-100 nM, with a dose-effect relationship in both cell models. On C11 cells, the ingenol compound 16A activates the latent HIV-1 with an $EC_{50}$ of 3.53 nM, while 760 nM for Prostratin; however on J-Lat-A10.6 cells, the ingenol compounds and their derivatives (such as, 16A, 16A-4A, 16A-5A, 16A-6A, 16A-12A, 16A-15A, 16A-17A) activate the latent HIV-1 with a lowest $EC_{50}$ of 4.06 nM, while 860 nM for Prostratin.

In both latent cell lines, the $EC_{50}$ of the ingenol compounds and their derivatives were more than 200 times lower than that of Prostratin. It can be seen that the ingenol compounds and their derivatives were extremely active in activating latent HIV-1. High levels of HIV-1 activation can be induced at very low concentrations.

EXAMPLE 10

Activation of the Ingenol Compounds in Peripheral Blood Resting CD4+ T Cells The resting CD4+ T cells isolated from the peripheral blood of 5 AIDS patients were treated with 5 μg/ml PHA (phytohemagglutinin) (positive control) and 0.005 μM compound 16A for 18 h, and then HIV-1 mRNA was extracted from resting CD4+ T cells and the medium, real-time PCR was used to detect the change of HIV-1 mRNA expression level in resting CD4+ T cells and medium, respectively.

The results were shown in FIG. 5. The results showed that the intracellular activated HIV-mRNA after treatment with compound 16A was significantly higher than that in the control and PHA treated cells, indicating that compound 16A effectively activated the latent HIV virus. In all of the experimental cases, the effective activation of latent HIV could be observed in most patients.

In addition, after the treatment of the cells in the known HIV-infected latent reservoir with compound 16A and then antiretroviral drugs were administered, the number of viral latent reservoir treated with compound 16A was found to be significantly lower than that of untreated viral latent reservoir.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A compound represented by formula (II), or a pharmaceutically acceptable salt thereof

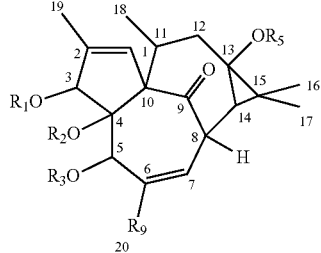

II wherein,
$R_1$ is H, or $COCH(CH_3)CH(CH_3)_2$;
$R_2$ is H, $COCH(CH_3)CH(CH_3)_2$ or substituted or unsubstituted $OCC_6H_5$;
$R_3$ is H, $COCH(CH_3)CH(CH_3)_2$ or substituted or unsubstituted $OCC_6H_5$;
$R_5$ is H, $COCH_3$, $OCH_2CH_3$ or $CO(CH_2)_{10}CH_3$;
$R_9$ is $CH_2OR_4$ or $—C(O)R_{10}$; wherein $R_4$ is H, $COCH_3$, $CH_2CH_3$, $OCH_2CH_3$, $CO(CH_2)_{10}CH_3$ or $CO(CH_2)_{14}CH_3$; and $R_{10}$ is selected from the group consisting of: H, $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;
or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;
wherein "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, and $C_2$-$C_6$ alkynyl;
provided that, $R_1$, $R_2$, $R_3$ and $R_4$ are not simultaneously H; and when $R_1$ is $COCH(CH_3)CH(CH_3)_2$ and both of $R_2$ and $R_3$ are H, $R_4$ is $OCH_2CH_3$, $CO(CH_2)_{10}CH_3$ or $CO(CH_2)_{14}CH_3$.

2. The compound or a pharmaceutically acceptable salt thereof of claim 1, wherein the compound has a structure as shown in formula IIa or formula IIb:

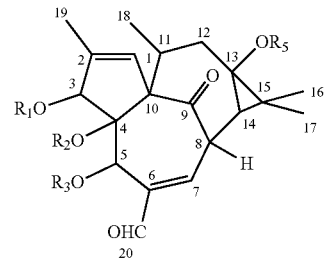

IIa

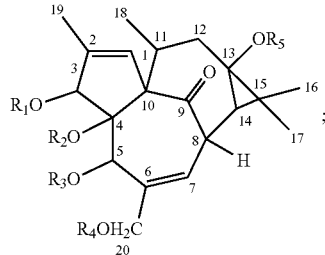

IIb and $R_1$, $R_2$, $R_3$, $R_4$ and $R_5$ are defined as formula II.

3. A pharmaceutical composition comprising:
(a1) a first active ingredient for interfering with the HIV virus latency, which is a compound of formula I or an acceptable salt thereof;
(a2) a second active ingredient for inhibiting replication of HIV virus, which is an antiretroviral drug; and
(b) a pharmaceutically acceptable carrier;

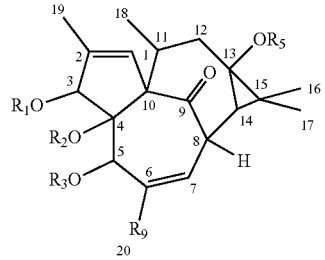

I wherein
$R_1$ is H or substituted or unsubstituted $COCH(CH_3)CH(CH_3)_2$;
$R_2$ is H, substituted or unsubstituted $COCH(CH_3)CH(CH_3)_2$ or substituted or unsubstituted $OCC_6H_5$;
$R_3$ is H, substituted or unsubstituted $COCH(CH_3)CH(CH_3)_2$ or substituted or unsubstituted $OCC_6H_5$;
$R_5$ is H, $COCH_3$, $OCH_2CH_3$ or $CO(CH_2)_{10}CH_3$;
$R_9$ is selected from the group consisting of: $CH_2OR_4$ and $—C(O)R_{10}$; wherein $R_4$ is selected from H, $COCH_3$, $OCH_2CH_3$, $CH_2CH_3$, $CO(CH_2)_{10}CH_3$ and $CO(CH_2)_{14}CH_3$; and $R_{10}$ is selected from the group consisting of: H, substituted or unsubstituted $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;
or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, and $C_2$-$C_6$ alkynyl;

provided that, $R_1$, $R_2$, $R_3$ and $R_4$ are not simultaneously H; and when $R_1$ is $COCH(CH_3)CH(CH_3)_2$ and both of $R_2$ and $R_3$ are H, $R_4$ is selected from $OCH_2CH_3$, $CO(CH_2)_{10}CH_3$ and $CO(CH_2)_{14}CH_3$.

4. A method for (a) interfering with the HIV virus latency or (b) inducing a HIV proviral expression in a latently infected cell of the HIV virus, comprising the steps of: in the presence of a compound of formula II or a pharmaceutically acceptable salt thereof, culturing the latently infected cell of the HIV virus to cause the expression of the latent HIV provirus, thereby activating the latent HIV virus;

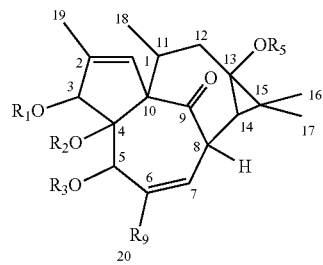

II wherein, $R_1$ is H, or $COCH(CH_3)CH(CH_3)_2$;

$R_2$ is H, $COCH(CH_3)CH(CH_3)_2$ or substituted or unsubstituted $OCC_6H_5$;

$R_3$ is H, $COCH(CH_3)CH(CH_3)_2$ or substituted or unsubstituted $OCC_6H_5$;

$R_5$ is H, $COCH_3$, $OCH_2CH_3$ or $CO(CH_2)_{10}CH_3$;

$R_9$ is $CH_2OR_4$ or —$C(O)R_{10}$; wherein $R_4$ is H, $COCH_3$, $CH_2CH_3$, $OCH_2CH_3$, $CO(CH_2)_{10}CH_3$ or $CO(CH_2)_{14}CH_3$; and $R_{10}$ is selected from the group consisting of: H, $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;

or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, and $C_2$-$C_6$ alkynyl;

provided that, $R_1$, $R_2$, $R_3$ and $R_4$ are not simultaneously H; and when $R_1$ is $COCH(CH_3)CH(CH_3)_2$ and both of $R_2$ and $R_3$ are H, $R_4$ is $OCH_2CH_3$, $CO(CH_2)_{10}CH_3$ or $CO(CH_2)_{14}CH_3$.

5. A method of treating a latent infection of an HIV virus, comprising the steps of:

(I) administering to a subject in need thereof a formulation comprising a compound of formula II or a pharmaceutically acceptable salt thereof;

(II) administering to the subject a formulation comprising an antiretroviral drug, 5-50 hours, preferably 10-48 hours, more preferably 15-24 hours after the step (I); and optionally, (III) repeating steps (I)-(II);

thereby treating the latent infection of HIV virus;

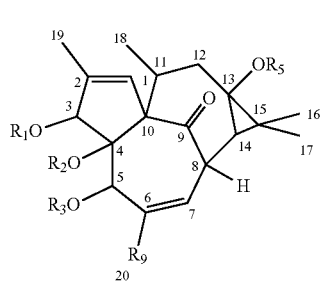

II wherein, $R_1$ is H, or $COCH(CH_3)CH(CH_3)_2$;

$R_2$ is H, $COCH(CH_3)CH(CH_3)_2$ or substituted or unsubstituted $OCC_6H_5$;

$R_3$ is H, $COCH(CH_3)CH(CH_3)_2$ or substituted or unsubstituted $OCC_6H_5$;

$R_5$ is H, $COCH_3$, $OCH_2CH_3$ or $CO(CH_2)_{10}CH_3$;

$R_9$ is $CH_2OR_4$ or —$C(O)R_{10}$; wherein $R_4$ is H, $COCH_3$, $CH_2CH_3$, $OCH_2CH_3$, $CO(CH_2)_{10}CH_3$ or $CO(CH_2)_{14}CH_3$; and $R_{10}$ is selected from the group consisting of: H, $C_1$-$C_6$ alkyl, $C_2$-$C_6$ alkenyl, $C_2$-$C_6$ alkynyl, $C_1$-$C_6$ alkoxy, —OH, $C_1$-$C_6$ ester group, and a combination thereof;

or, any one or two of $R_1$ and $R_2$, $R_2$ and $R_3$, $R_3$ and $R_9$ respectively and independently forms a 5-7 membered substituted or unsubstituted heterocycle with an adjacent ring carbon atom, and the heterocycle contains 2-3 oxygen atoms and 0-1 heteroatoms selected from N or S;

wherein "substituted" means that H in a group is substituted with one or more substituents selected from the group consisting of: halogen, $C_1$-$C_6$ alkyl, $C_1$-$C_6$ haloalkyl, $C_2$-$C_6$ alkenyl, and $C_2$-$C_6$ alkynyl;

provided that, $R_1$, $R_2$, $R_3$ and $R_4$ are not simultaneously H; and when $R_1$ is $COCH(CH_3)CH(CH_3)_2$ and both of $R_2$ and $R_3$ are H, $R_4$ is $OCH_2CH_3$, $CO(CH_2)_{10}CH_3$ or $CO(CH_2)_{14}CH_3$.

6. The method of claim 4, wherein the method further comprises the step of activating a latent HIV virus.

7. The method of claim 4, wherein the method further comprises the step of inhibiting and/or killing a latent HIV virus.

8. The pharmaceutical composition of claim 3, wherein any one group of $R_1$ and $R_2$, $R_2$ and $R_3$, $R_3$ and $R_9$ respectively and independently forms a 5-7 membered substituted or unsubstituted heterocycle containing 2-3 oxygen atoms and 0-1 heteroatoms selected from N or S.

9. The pharmaceutical composition of claim 3, wherein any two groups of $R_1$ and $R_2$, $R_2$ and $R_3$, $R_3$ and $R_9$ respectively and independently form a 5-7 membered substituted or unsubstituted heterocycle containing 2-3 oxygen atoms and 0-1 heteroatoms selected from N or S.

10. The pharmaceutical composition of claim 3, wherein $R_2$ and $R_3$ form a 5-7 membered substituted or unsubstituted heterocycle with an adjacent ring carbon atom.

11. The pharmaceutical composition of claim 3, wherein $R_2$ and $R_3$ form a 5-6 membered substituted or unsubstituted heterocycle with an adjacent ring carbon atom.

12. The pharmaceutical composition of claim 3, wherein $R_1$ and $R_2$ form a 5-7 membered substituted or unsubstituted heterocycle with an adjacent ring carbon atom.

13. The pharmaceutical composition of claim 3, wherein $R_1$ and $R_2$ form a 5-6 membered substituted or unsubstituted heterocycle with an adjacent ring carbon atom.

14. The pharmaceutical composition of claim 3, wherein $R_3$ and $R_9$ form a 5-7 membered substituted or unsubstituted heterocycle with an adjacent ring carbon atom.

15. The pharmaceutical composition of claim 3, wherein $R_3$ and $R_9$ form a 5-6 membered substituted or unsubstituted heterocycle with an adjacent ring carbon atom.

16. The pharmaceutical composition of claim 3, wherein the heterocycle is a 5-6 membered heterocycle containing 2 oxygen atoms with 1-2 $C_1$-$C_3$ alkyl.

17. The pharmaceutical composition of claim 3, wherein the heterocycle is selected from the group consisting of:

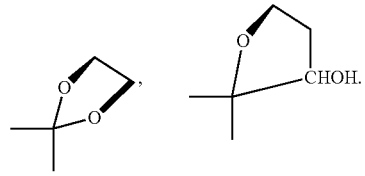

18. The pharmaceutical composition of claim 3, wherein the compound is selected from the group consisting of:

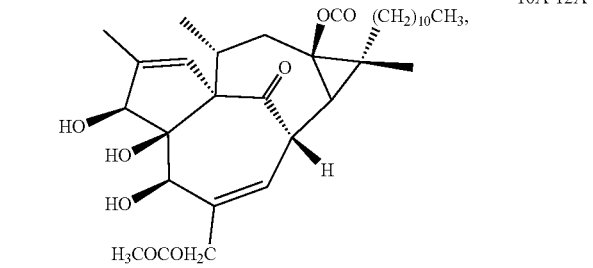

16A-12A

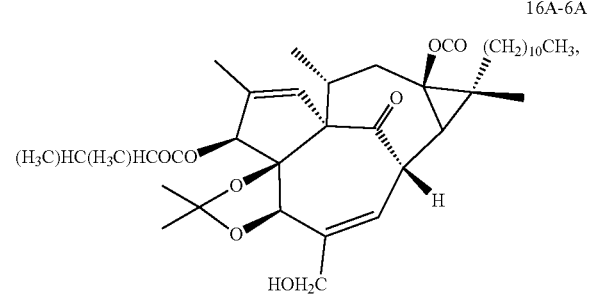

16A-6A

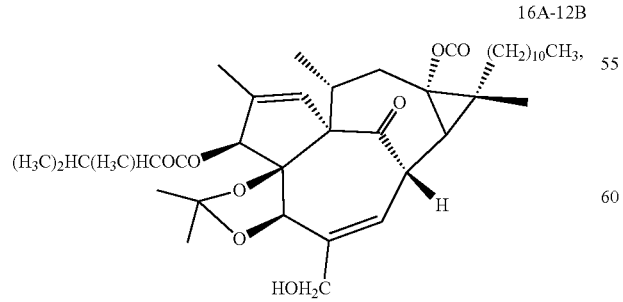

16A-12B

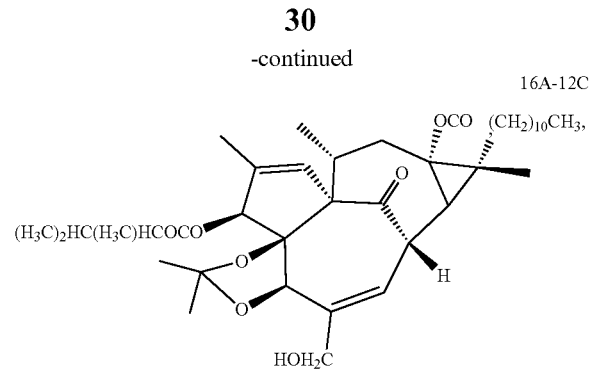

16A-12C

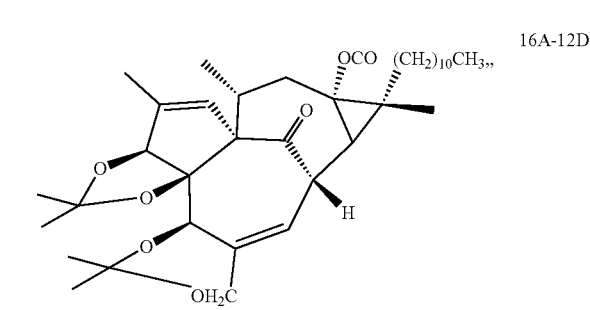

16A-12D

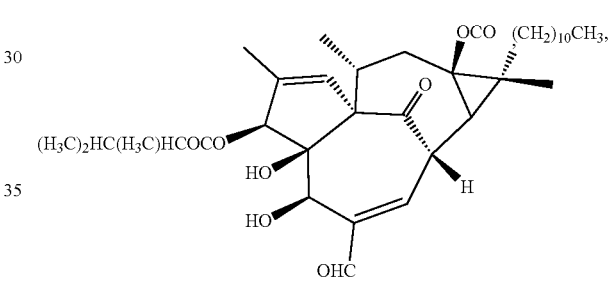

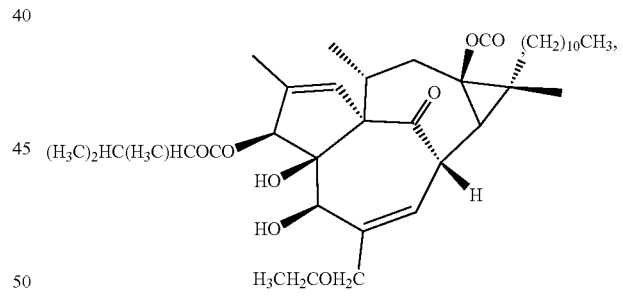

and

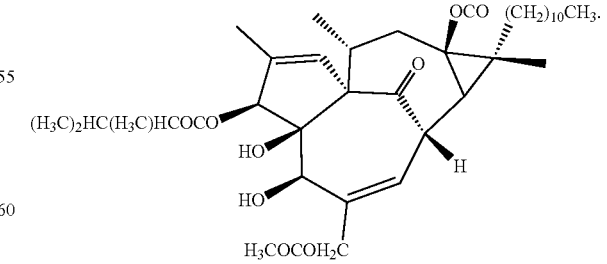

* * * * *